(12) United States Patent
Griffiths et al.

(10) Patent No.: US 6,433,234 B1
(45) Date of Patent: Aug. 13, 2002

(54) PROCESS FOR THE PRODUCTION OF OLEFINS

(75) Inventors: David Charles Griffiths; Cord Oehlers, both of Surrey; Ian Allan Beattie Reid, London, all of (GB)

(73) Assignee: BP Chemicals Limited, London (GB)

( * ) Notice: Subject to any disclaimer, the term of this patent is extended or adjusted under 35 U.S.C. 154(b) by 60 days.

(21) Appl. No.: 09/659,510

(22) Filed: Sep. 11, 2000

Related U.S. Application Data

(63) Continuation of application No. PCT/GB99/02965, filed on Sep. 7, 1999.

(30) Foreign Application Priority Data

Sep. 8, 1998 (GB) ............................................. 9819603

(51) Int. Cl.⁷ ................................................. C07C 4/06
(52) U.S. Cl. ....................... 585/324; 585/651; 585/652; 585/653
(58) Field of Search ................................. 585/651, 652, 585/653, 324

(56) References Cited

U.S. PATENT DOCUMENTS

| | | | | |
|---|---|---|---|---|
| 4,264,435 A | * | 4/1981 | Read et al. ................. | 208/129 |
| 4,527,003 A | * | 7/1985 | Okamoto et al. ........... | 208/107 |
| 4,655,904 A | * | 4/1987 | Okamoto et al. ........... | 208/106 |
| 5,105,052 A | * | 4/1992 | Freide et al. ............... | 585/651 |
| 5,382,741 A | * | 1/1995 | Astbury et al. ............. | 585/652 |
| 5,625,111 A | * | 4/1997 | Astbury et al. ............. | 585/648 |
| 5,663,473 A | * | 9/1997 | Griffiths et al. ............ | 134/2 |

FOREIGN PATENT DOCUMENTS

| | | |
|---|---|---|
| EP | 0 332 289 | 9/1989 |
| WO | WO 94/04632 | 3/1994 |

* cited by examiner

Primary Examiner—Walter D. Griffin
(74) Attorney, Agent, or Firm—Finnegan, Henderson, Farabow, Garrett and Dunner, L.L.P.

(57) ABSTRACT

A process for the production of olefins from a hydrocarbon comprising the steps of: a) providing a first feed stream comprising a gaseous fuel and an oxygen-containing gas; b) contacting the first feed stream with a first catalyst under conditions so as to produce a product stream and unreacted oxygen; c) providing a second feed stream of hydrocarbon feedstock; and d) contacting the second feed stream, the product stream of step b) and the unreacted oxygen step b) with a second catalyst which is capable of supporting oxidation, thereby consuming at least a part of the unreacted oxygen to produce an olefin product.

17 Claims, No Drawings

PROCESS FOR THE PRODUCTION OF OLEFINS

RELATED APPLICATIONS

This application is a continuation of international application No. PCT/GB99/02965 filed Sep. 7, 1999.

BACKGROUND OF THE INVENTION

The present invention relates to a process for the production of olefins. Olefins such as ethylene and propylene may be produced by the catalytic dehydrogenation or cracking of a hydrocarbon feed. In this application the term "cracking" will be used to embrace both these chemical reactions. In an auto-thermal cracking process, a hydrocarbon feed is mixed with an oxygen-containing gas and contacted with a catalyst capable of supporting combustion beyond the fuel rich limit of flammability. The hydrocarbon feed is partially combusted and the heat produced is used to drive the cracking reaction.

An example of an auto-thermal cracking process is described in EP 0 332 289. The document describes the use of a paraffinic feed of, for example, ethane, propane and/or butane which is mixed with oxygen, and cracked to produce an olefinic mixture. The cracking reaction is endothermic and is carried out at elevated temperatures above 800° C.

The energy required for the cracking reaction is provided by combustion of a part of the feed. The feed may also be preheated but the temperature is limited due to the risk of auto ignition. It is desirable to maximise the amount of feed available for cracking by reducing the amount of feed required for combustion.

It is among the objects of the present invention to find an additional or alternative source of heat to drive the cracking step of the auto-thermal cracking process.

SUMMARY OF THE INVENTION

This is achieved by providing an auto-thermal process comprising a preliminary heat-generating step. In this step, a gaseous fuel such as a hydrocarbon reacts with oxygen in an exothermic reaction in the presence of a catalyst. The reaction conditions are controlled to ensure that not all of the oxygen is consumed during this process. The thermal energy produced by the reaction heats the unreacted oxygen, thereby providing an additional source of heat to drive the cracking of the hydrocarbon feedstock.

According to the present invention, there is provided a process for the production of olefins from a hydrocarbon, said process comprising the steps of:

a) providing a first feed stream comprising a gaseous fuel and an oxygen-containing gas, b) contacting said first feed stream with a first catalyst under conditions so as to produce a product stream and unreacted oxygen, c) providing a second feed stream comprising a hydrocarbon feedstock, and d) contacting said second feed stream, said product stream of step b) and said unreacted oxygen of step b) with a second catalyst which is capable of supporting oxidation, thereby consuming at least a part of the unreacted oxygen to produce an olefin product.

According to a preferred embodiment of the present invention, there is provided a process for the production of olefins from a hydrocarbon, said process comprising the steps of:

a) providing a first feed stream comprising a gaseous hydrocarbon and an oxygen-containing gas, b) contacting said first feed stream with a first catalyst under conditions so as to produce a product stream and unreacted oxygen, c) providing a second feed stream comprising a hydrocarbon feedstock, and d) contacting said second feed stream, said product stream of step b) and said unreacted oxygen of step b) with a second catalyst which is capable of supporting oxidation, thereby consuming at least a part of the unreacted oxygen to produce an olefin product.

DETAILED DESCRIPTION OF THE INVENTION

The process of the present invention provides a means of minimising the amount of hydrocarbon feedstock consumed to generate the heat required to drive the cracking of the hydrocarbon feedstock. By reducing the amount of hydrocarbon consumed in this manner, a larger proportion of the hydrocarbon feedstock is available for conversion into olefinic products. This may result in higher olefin yields and enhanced selectivities towards the olefin product. The throughput through the reactor is also enhanced.

The process of the present invention also provides a means of maintaining the second catalyst at an elevated temperature. In doing so, non-volatile hydrocarbons are prevented from condensing on the catalyst and reducing the catalyst's activity. This allows a higher through put through the reactor. On heavy residue-containing feeds the process of the present invention provides the additional advantage of increasing the time on oil processing between catalyst decokes.

The gaseous fuel of the first feed stream is any gaseous fuel which is capable of reacting with oxygen in an exothermic reaction. Suitable examples include hydrocarbons, such as methane, ethane, propane and butane; with methane being preferred. Other suitable fuels include hydrogen, carbon monoxide, alcohols (eg methanol, ethanol), oxygenates and/or ammonia. Waste fuel streams may also be employed.

The oxygen-containing gas may comprise air, oxygen and/or an air/oxygen mixture. The oxygen-containing gas may be mixed with an inert gas such as nitrogen, helium or argon. Additional feed components such as hydrogen, carbon monoxide, carbon dioxide and steam may also be included.

The first feed stream is preferably fuel-rich with a fuel to oxygen ratio above the stoichiometric ratio required for complete combustion. For example, the fuel to oxygen ratio in the feed may be 1.5 to 4 times, preferably 3 times, the stoichiometric ratio required for complete combustion to carbon dioxide to water.

The gaseous fuel and oxygen-containing gas are contacted with a first catalyst under reaction conditions which are controlled to ensure that some of the oxygen in the first feed stream remains unreacted during step b). The thermal energy produced in step b) heats the unreacted oxygen, thereby providing part of the heat necessary for cracking the hydrocarbon feedstock in step d).

The reaction between the gaseous fuel and oxygen-containing gas may be a combustion reaction. Accordingly, gaseous fuel (eg hydrocarbon) in the first feed stream may react with oxygen to produce a product stream comprising oxides (eg carbon oxides) and water. In such an embodiment, a combustion catalyst is employed as the first catalyst. Suitable combustion catalysts include Group VIII metals such as platinum and/or palladium. The catalyst may comprise 0.1 to 5 wt % and, preferably, 0.25 to 3 wt %, of metal. It will be understood that the metal loadings of the catalyst may be selected to ensure that not all the oxygen in the first feed stream is consumed in step b).

In an alternative embodiment, the gaseous fuel of the first feed stream reacts with the oxygen-containing gas to produce synthesis gas. In this embodiment, a first feed stream comprising a hydrocarbon (e.g., methane) is employed, which reacts with oxygen to produce carbon monoxide and hydrogen. These gaseous products may react exothermically, for example with oxygen, thereby providing a further source of heat to drive the cracking reaction in step d). In this embodiment, the catalyst employed is one which is capable of supporting a synthesis gas production reaction. Suitable catalysts comprise rhodium, platinum, palladium, nickel or mixtures thereof. Preferably, a rhodium catalyst is used. The catalyst may comprise 0.1 to 5 wt % and, preferably, 0.25 to 3 wt %, of metal. As with combustion catalysts, the metal loadings of the catalyst may be varied to ensure that not all the oxygen in the first feed stream is consumed in step b).

In a further embodiment, a gaseous fuel is reacted with an oxygen-containing gas in a combustion reaction, and another gaseous fuel (which may or may not be the same as the first gaseous fuel) is reacted with an oxygen-containing gas to produce synthesis gas. Both these reactions are exothermic, and may provide part of the heat for driving the subsequent cracking reaction in step d). In at least one of these reactions, however, not all of the oxygen-containing gas employed is consumed. At least part of this unreacted oxygen is consumed in step d) to produce the olefin product of the present invention. The first catalysts of present invention may be supported. Suitable catalyst supports include a range of ceramic and metal supports, with alumina supports being preferred. The support may be in the form of spheres or other granular shapes, and may be present as a thin layer or wash coat on another substrate. Preferably, the substrate is a continuous multi-channel ceramic structure such as a foam or a regular channelled monolith. In a preferred embodiment, a gamma alumina coated alpha alumina. Alternatively, zirconia or a gamma alumina coated lithium aluminium silicate foam support may be employed. The nature of the catalyst support may be varied to ensure that not all the oxygen in the first feed stream is consumed in step b).

The first feed stream may be contacted with the first catalyst at a temperature of between 600 and 1200° C., preferably between 700 and 1100° C., and most preferably between 950 and 1050° C.

The first feed stream may be contacted with the first catalyst at any suitable pressure, e.g. atmospheric or elevated pressure. If elevated pressures are employed, any pressure above 1 bara may be used. Suitable elevated pressures range from 1.1 to 50 bara, for example, 5 to 50 bara, although pressures of 1.1 to 8 bara, for example, 1.8 bara are preferred. It will be understood that the precise pressures employed will. vary depending on the specific reaction conditions and gaseous fuels employed.

The process of the present invention may be carried out in a reactor comprising at least two reaction zones, which are in fluid communication with one another. Where a two-reaction-zone reactor is employed, the first reaction zone is provided with the first catalyst, whilst the second reaction zone is provided with the second catalyst. Accordingly, when the first feed stream is introduced into the first reaction zone under suitable reaction conditions, the reaction of step b) takes place. The unreacted oxygen produced in step b) is then introduced into the second reaction zone, where it comes into contact with the second catalyst and the second feed stream as described in step d).

In one embodiment, the present invention is carried out in a reactor having a main chamber, and a side chamber. The side chamber may define the first reaction zone, and the main reaction chamber the second reaction zone, or vice-versa. In an alternative embodiment, the first and second reaction zones are defined by nested, generally concentric tubular housings. Preferably, the outer housing extends beyond the end of the inner housing, such that fluid entering the outer housing from the inner housing mixes with the second feed stream before coming into contact with the second catalyst. Advantageously, mixing means may be provided between the first and second reaction zones. Suitable mixing means include a grid, a perforated plate, and/or a baffle plate.

The rate at which the first feed stream may be introduced into the first reaction zone may be measured in terms of gas hourly space velocity ($h^{-1}$). This is defined as:

$$GHSV = \text{volume of total feed}/(\text{time} \times \text{volume of catalyst bed})$$

Suitably, the first feed stream is introduced at a gas hourly space velocity of greater than 10,000 $h^{-1}$, preferably above 100,000 $h^{-1}$ and most preferably, greater than 300,000 $h^{-1}$. It will be understood that the optimum gas hourly space time velocity will depend upon the pressure and nature of the feed composition. In general, high superficial linear velocities are preferred to ensure that not all of the oxygen in the first feed stream is consumed.

In step d) of the present invention, the unreacted oxygen and product stream of step b) are contacted with a second catalyst together with the second feed stream. In the ensuing reaction, at least a part of the unreacted oxygen is consumed, and an olefinic product is produced. Preferably, substantially all of the unreacted oxygen is consumed.

As mentioned above, this reaction may occur in a second reaction zone of a reactor. In such an embodiment, the unreacted oxygen and product stream of step c) are introduced into the second reaction zone at a velocity of greater than 1 m/s, preferably greater than 3 m/s calculated under feed conditions. These velocities are sufficiently high to prevent flashback into the first reaction zone. The product stream from step b) may be pre-mixed with the second feed stream and the resulting reactant mixture may be contacted with the second catalyst. Suitable mixing means include a baffle plate, a grid or a perforated plate. Alternatively, the unreacted oxygen and product stream of step c) may be contacted with the second catalyst together with the second feed stream, in the absence of a pre-mixing step.

The second feed stream may comprise any suitable hydrocarbon. For example, gaseous hydrocarbons, heavy hydrocarbons or mixtures thereof may be employed. Suitable gaseous hydrocarbons include ethane, propane, butane and mixtures thereof. Suitable heavy hydrocarbons include naptha, gas oil, vacuum gas oil, refinery residues, atmospheric residues, vacuum residues, and crude and fuel oils. Additional feed components such as hydrogen, nitrogen, carbon monoxide, carbon dioxide and steam may also be included in the second feed stream. Hydrogen and/or carbon monoxide may react with the unreacted oxygen present to produce additional heat for driving the cracking process.

Heavy hydrocarbon feed may be contacted with the second catalyst in a liquid or vaporised state. Where the hydrocarbon is contacted as a liquid, the hydrocarbon may be introduced to the second catalyst as a spray of droplets so that partial vaporisation and homogeneous mixing may result. In an embodiment of the invention, liquid hydrocarbon is introduced to the second catalyst using a nozzle.

In the second feed stream, a gaseous hydrocarbon may be alternated with a heavy hydrocarbon, as the hydrocarbon feed stock. Conventionally, this is done to limit exposure of the catalyst to heavier, less volatile hydrocarbons, which may condense on the catalyst and reduce its activity. With the present invention, the second catalyst is maintained at an elevated temperature by virtue of step b). Thus, the present invention allows the catalyst to be contacted with heavy hydrocarbons for longer periods of time, allowing a higher throughput through the reactor. The efficiency of the heavy hydrocarbon cracking process is thus increased. The second feed stream is introduced at a gas hourly space velocity of greater than 10,000 $h^{-1}$, preferably above 20,000 $h^{-1}$ and most preferably, greater than 100,000 $h^{-1}$. It will be understood, however, that the optimum gas hourly space time velocity will depend upon the pressure and nature of the feed composition.

The hydrocarbon feed in the second feed stream may be cracked into olefins such as ethene, propene, butene and pentene or a mixtures thereof The second catalyst is a catalyst which is suitable for catalysing an auto-thermal cracking process. The catalytic metal is typically platinum. In one embodiment of the present invention, a second metal such as copper, tin, and/or palladium is added to the platinum. Preferably, platinum and/or palladium containing catalyst is used. The catalyst may comprise 0.1 to 5 wt %, preferably 0.25 to 1 wt % of metal.

The second catalyst is preferably supported. Suitable catalyst supports include a wide range of ceramic and metal supports, with alumina supports being preferred. The support may be in the form of spheres or other granular shapes, and may be present as a thin layer or wash coat on another substrate. Preferably, the substrate is a continuous multichannel ceramic structure such as a foam or a regular channelled monolith. In a preferred embodiment, a gamma alumina coated alpha alumina support is employed. However, a gamma alumina coated lithium aluminium silicate (LAS) foam support or a zirconia ceramic foam may also be employed. In an alternative embodiment, the second catalyst is a metal oxide compound having a perovskite structure.

Advantageously, heat may also be supplied by pre-heating the hydrocarbon in the second feed stream. In the present invention, oxygen and the crackable hydrocarbons may be introduced separately into the cracking or second reaction zone. Accordingly, the temperature of the pre-heated stream need not be limited by autoignition considerations, and the hydrocarbon feedstock in the second feedstream may be heated to a temperature of 200° C. to 600° C., and preferably to 500° to 600° C.

The cracking reaction may be suitably carried out at a temperature of between 600 and 1200° C., preferably between 850 and 1050° C. and most preferably, between 900 and 1000° C. It will be understood that the optimum temperature will depend upon the feed mixture and operating pressure.

The cracking reaction may be carried out at atmospheric or elevated pressure. Suitable elevated pressures range from 1.1 to 50 bara, for example, 5 to 50 bara, although pressures of 1.1 to 8 bara, for example, 1.8 bara are preferred. It will be understood that the precise pressures employed will vary depending on the specific reaction conditions and gaseous fuels employed.

Where the cracking reaction is carried out at elevated pressure, the reaction products may be quenched as they emerge from the reaction chamber to avoid further reactions taking place. The reaction product may be quenched within 50 milliseconds from formation. It will be understood, however, that the time required between product formation and the act of quenching will depend upon reaction conditions such as pressure and temperature.

The products may be quenched using rapid heat exchangers of the type familiar in steam cracking technology. Additionally or alternatively, a direct quench may be employed. Suitable quenching fluids include water and hydrocarbons such as ethane or naphtha.

The process of the present invention may be carried out in a fluid bed, fixed bed or spouted bed reactor. Fixed bed reactors are preferred.

Any coke produced in the process of the present invention may be removed by mechanical means, or using one of the decoking methods described in EP 0 709 446, incorporated herein by reference.

These and other aspects of the present invention will now be described with reference to the following Examples.

EXAMPLE 1

In this Example, a metal reactor comprising i) a first reaction zone in the form of a side reaction chamber (inner diameter 18 mm), and ii) a second reaction zone in the form of a main reaction chamber (inner diameter 35 mm) was employed. The side reaction chamber was connected to the main reaction chamber via an inlet.

Methane, oxygen, hydrogen co-feed and nitrogen were introduced into the side reaction chamber at feed rates of about 8.2 g/min, 13.6 g/min, 0.4 g/min and 1.1 g/min, respectively. Ethane and nitrogen co-feed were introduced into the main reaction chamber at rates of about 22.5 to 24.48 g/min, and 1.1 to 1.3 g/min, respectively. The ethane was pre-heated between 200° and 500° C.

A side catalyst in the form of a 0.5 wt % Pt/0. 1 wt % Pd-loaded LAS (lithium alumina silicate) monolith (15 mm diameter×30 mm length, 10 ppi) was positioned in the side reaction chamber adjacent the inlet connecting the side and main chambers. The side feed stream was contacted with the side catalyst to produce a product stream and unreacted oxygen. The properties of the first catalyst, e.g. catalyst length, metal loading, porosity, were selected to ensure that sufficient unreacted oxygen was present in the stream entering the main reaction chamber to support an auto-thermal cracking reaction.

A main catalyst in the form of a catalyst support, lithium alumina silicate (LAS) foam loaded with 1.0/0.2 wt % Pt/Pd (28 mm diameter×15 mm length, 30 ppi) was located in the main reaction chamber. The main catalyst was positioned below the side reaction chamber/main reaction chamber interface to allow sufficient mixing between the product stream from the side reaction chamber and the main feed stream. The resulting mixture is contacted with the main catalyst thereby consuming substantially all of the unreacted oxygen to produce an olefinic product comprising ethene.

Both reaction chambers contained quartz inserts to minimise heat losses. The reactors were operated at close to atmospheric pressure.

Feed rates, molar ratios, reaction conditions and experimental results are shown in Table 1a. Ethene selectivity is defined as ratio of mass ethene over mass ethane utilised. Product Composition (wt % C) is defined as ratio of weight of carbon in product over total weight of carbon in feed.

TABLE 1a

| Total Flow nl/min | Ethane Preheat (° C.) | Mixed Feed first stream nl/min | Ethane feed second stream nl/min | $C_2H_6/O_2$ | $CH_4/O_2$ | $H_2/O_2$ | $N_2/O_2$ | O/C Mass Ratio | Product Temperature (° C.) | Ethane Conversion (wt %) | Methane Conversion (wt. %) | Ethene Selectivity (%) |
|---|---|---|---|---|---|---|---|---|---|---|---|---|
| 43.62 | 226 | 26.82 | 16.8  | 1.76 | 1.2 | 0.41 | 0.2 | 0.57 | 868 | 72   | −1.52 | 65 |
| 46.53 | 207 | 26.76 | 19.71 | 2.07 | 1.2 | 0.41 | 0.2 | 0.50 | 845 | 58.9 | −0.26 | 67 |
| 45.10 | 359 | 26.82 | 18.28 | 1.92 | 1.2 | 0.41 | 0.2 | 0.53 | 861 | 69.1 | −3.19 | 67 |
| 43.62 | 454 | 26.82 | 16.8  | 1.76 | 1.2 | 0.41 | 0.2 | 0.57 | 896 | 77.8 | −5.01 | 65 |
| 44.45 | 440 | 26.76 | 17.63 | 1.85 | 1.2 | 0.41 | 0.2 | 0.54 | 877 | 71.5 | −1.5  | 67 |

| | | | Product Composition wt % C | | | | |
|---|---|---|---|---|---|---|---|
| $C_2H_6$ | $C_2H_4$ | $C_2H_2$ | $CH_4$ | CO | $CO_2$ | $C_3/C_4/C_5$ | $C_6H_6$ |
| 20.92 | 37.26 | 0.27 | 25.75 | 11.01 | 1.42 | 3.31 | 0.07 |
| 31.88 | 32.74 | 0    | 22.52 | 8.3   | 1.37 | 3.14 | 0.05 |
| 23.5  | 37.65 | 0.2  | 24.65 | 9.92  | 1.13 | 3.13 | 0.11 |
| 16.59 | 40.32 | 0.61 | 26.64 | 11.86 | 1.04 | 2.9  | 0.04 |
| 21.52 | 38.87 | 0.4  | 24.83 | 10.26 | 0.96 | 3.1  | 0.06 |

Comparative Example

In this comparative example, a metal reactor having a single reaction chamber was employed. The chamber was loaded with a 0. wt %Pd/0.2 wt % Pt on LAS catalyst which was identical to the main Pd/Pt catalyst of Example 1. Ethane, oxygen and nitrogen co-feed were introduced into the reaction chamber at the feed rates listed in Table 1b below. The reactants were preheated to a temperature of 150° C.

The pre-heated reactants were reacted in the presence of the Pd/Pt catalyst to produce an olefinic product comprising ethene. Table 1b compares the selectivities and etheneloxygen mass ratios achieved in Example 1 with those achieved in the Comparative Example.

Table 1b shows the advantages in terms of selectivity and ethene/oxygen mass ratio in comparison to experiments carried out with a metal reactor comprising only a main reaction chamber.

TABLE 1b

| | Gas operation with main and side reaction chamber | | | | Gas operation with main reaction chamber | | |
|---|---|---|---|---|---|---|---|
| | 1 | 2 | 3 | 4 | 1 | 2 | 3 |
| Preheat(° C.) | 210 | 359 | 454 | 440 | 150 | 150 | 150 |
| Feed flow rates (g/min) | | | | | | | |
| Methane  | 8.16 | 8.16 | 8.16 | 8.16 | 0 | 0 | 0 |
| Hydrogen | 0.35 | 0.35 | 0.35 | 0.35 | 0 | 0 | 0 |

TABLE 1b-continued

| | Gas operation with main and side reaction chamber | | | | Gas operation with main reaction chamber | | |
|---|---|---|---|---|---|---|---|
| | 1 | 2 | 3 | 4 | 1 | 2 | 3 |
| Ethane   | 22.5  | 24.48 | 22.5  | 23.61 | 21.56 | 15.21 | 15.21 |
| Oxygen   | 13.63 | 13.63 | 13.63 | 13.63 | 12.0  | 12.0  | 8.39  |
| Nitrogen | 2.44  | 2.44  | 2.44  | 2.44  | 4.15  | 2.89  | 3.04  |
| Ethane Conversion (%) | 72 | 69.1 | 77.8 | 71.5 | 77.8 | 73.3 | 71.8 |
| Ethene Selectivity (%) | 65.0 | 67 | 65 | 67 | 59.6 | 60.5 | 59.8 |
| Ethene/Oxygen | 0.77 | 0.83 | 0.83 | 0.83 | 0.83 | 0.81 | 0.78 |

EXAMPLE 2

This Example was carried out using the reactor and main catalyst of Example 1. However, instead of a Pt/Pd side catalyst, a 30 ppi, approximately 2 wt % Rh catalyst (15 mm diameter×15 mm length) was employed.

Reaction conditions and experimental results are tabulated in Table 2.

TABLE 2

| Total Flow (nl/min) | Ethane Preheat (° C.) | $C_2H_6/O_2$ | $H_2/O_2$ | $N_2/O_2$ | $CH_4/O_2$ | $O_2/C$ Mass Ratio | Product Temperature (° C.) | Ethane Conversion (wt %) | Ethene Selectivity[1] (%) | $C_2H_4$ | $C_2H_2$ | $CH_4$ | Yield (wt % C) CO | $CO_2$ | $C_3/C_4$ | $C_6H_6$ | $CH_4$ |
|---|---|---|---|---|---|---|---|---|---|---|---|---|---|---|---|---|---|
| 32.42 | 355 | 2.0  | 0    | 0.27 | 1.78 | 0.46 | 808 | 45.1 | 78.2 | 26.18 | 0.0 | 24.84 | 9.59  | 1.72 | 1.75 | 0    | 19.1 |
| 36.46 | 503 | 1.96 | 0.59 | 0.26 | 1.78 | 0.47 | 842 | 47.5 | 80.0 | 28.31 | 0.0 | 24.07 | 10.19 | 1.24 | 1.65 | 0    | 22   |
| 39.97 | 501 | 2.22 | 0.04 | 0.21 | 1.39 | 0.46 | 852 | 59.5 | 71.7 | 34.81 | 0.0 | 22.01 | 8.93  | 1.41 | 1.57 | 0.04 | 7.5  |
| 39.02 | 504 | 1.85 | 0    | 0.19 | 1.26 | 0.54 | 880 | 70.7 | 68.2 | 38.57 | 0.0 | 23.55 | 12.51 | 1.98 | 1.41 | 0    | 7    |

EXAMPLE 3

In this Example, a main stream comprising a heavy hydrocarbon oil was employed. As can be seen in Table 3, hydrocarbon feedstocks such as Forties Vacuum Residue, Arabian Light Vacuum Residue and Arabian Light Atmospheric Residue were employed. The Example was carried out using a reactor which was formed of a metal tube flanged at both ends and fitted with a quartz liner to minimise heat loss. The reactor comprises a first reaction zone in the form of a side reaction chamber (inner diameter 18 mm) This is connected at right angles to a second reaction zone in the form of a main reaction chamber (inner diameter 35 mm) via an inlet.

The side reaction chamber was provided with a catalyst (15 mm OD*depth of 30 mm, 10 ppi) which was supported on LAS foam. The foam support was loaded with 1.5 wt % Pt and 0.3 wt % Pd when Forties VR was employed in the main catalyst feed stream. In contrast, when Arabian Light Vacuum Residue and Arabian Light Atmospheric Residue were employed in the main feed stream, metal loadings of 0.25 wt % Pt and 0.05 wt % Pd were employed, respectively.

The main reaction chamber was provided with a catalyst bed (28 mm OD*30 mm depth, 10 ppi LAS foam) comprising 1.0 wt % Pt and 0.2 wt % Pd on LAS foam.

Methane, oxygen and hydrogen co-feed were introduced into the side reaction chamber at a rate of 8 g/min, 12.7 g/min and 0.5 g/min, respectively. These gases were contacted with the side catalyst to produce a product stream and unreacted oxygen. The properties of the first catalyst, e.g. catalyst length, metal loading, porosity, were selected to ensure that sufficient unreacted oxygen was present in the stream entering the main reaction chamber to support an auto-thermal cracking reaction.

Hydrocarbon oil was fed into the main reaction chamber using a gas assist hydraulic nozzle (0.6 mm/30 or 60 degree). Nitrogen (current gas) was fed at 1.5 ml/min into the nozzle through a $1/16^{th}$ inch tube immediately above a swirl chamber to produce an oil/gas mixture. The flow rate for the oil and nitrogen are approximately 33.0 g/min and 1.5 g/min, respectively.

The main catalyst was positioned approximately 50 mm from the nozzle and a conical spray of the gas/oil mixture is sprayed onto the catalyst at a conical angle of 30 or 60 degrees.

The distance between the side chamber inlet and the nozzle was approximately 50 mm. The length of the main reaction chamber exit pipe to the collection vessel was equivalent to a residence time between 100 to 150 ms dependent on temperatures.

Feed rates, molar ratios, reaction conditions and experimental results for different feedstocks are shown in Table 3.

We claim:

1. A process for the production of olefins from a hydrocarbon, said process comprising the steps of:
    a) providing a first feed stream comprising a gaseous fuel and an oxygen-containing gas,
    b) reacting the first stream by contacting said first feed stream with a first catalyst under conditions so as to produce a product stream and unreacted oxygen,
    c) providing a second feed stream comprising a hydrocarbon feedstock, and
    d) contacting said second feed stream, said product stream of step b) and said unreacted oxygen of step b) with a second catalyst which is capable of supporting oxidation, thereby consuming at least a part of the unreacted oxygen to produce an olefin product.

2. A process as claimed in claim 1, wherein the gaseous fuel is selected from the group consisting of a hydrocarbon, hydrogen, carbon monoxide, an alcohol, an oxygenate, ammonia and mixtures thereof.

3. A process as claimed in claim 2, wherein the gaseous fuel is selected from the group consisting of methane, ethane, propane, butane and mixtures thereof.

4. A process as claimed in claim 3, wherein the reaction between the gaseous fuel and oxygen-containing gas is a synthesis gas producing reaction.

5. A process as claimed in claim 1, wherein the reaction between the gaseous fuel and oxygen-containing gas is a combustion reaction.

6. A process as claimed in claim 1, wherein the first catalyst comprises at least one metal selected from group consisting of rhodium, platinum, palladium and nickel.

7. A process as claimed in claim 1 wherein the gaseous fuel to oxygen ratio in the first feed stream is 1.5 to 4 times the stoichiometric ratio required for complete combustion to carbon dioxide to water.

8. A process as claimed in claim 1, which is carried out in a reactor comprising at least one first reaction zone and at least one second reaction zone which are in fluid communication with one another.

9. A process as claimed in claim 8, wherein the first reaction zone is provided with the first catalyst, and the second reaction zone is provided with the second catalyst.

10. A process as claimed in claim 9, wherein the reactor comprises a main chamber and a side chamber, and wherein one of said chambers defines the first reaction zone, and the other of said chambers defines the second reaction zone.

11. A process as claimed in claim 9, wherein the first and second reaction zones are defined by at least two nested tubular housings.

12. A process as claimed in claim 11, wherein the outer of said housings extends beyond the end of the inner of said housings, such that fluid entering said outer housing from

TABLE 3

| Feedstock | Total Gas Flow (nl/min) | $CH_4/O_2$ | $N_2/O_2$ | $O_2/C$ Mass Ratio | Main Catalyst Temperature (° C.) | Forties VR Conversion (wt %) | $C_2H_4$ | $C_2H_2$ | $CH_4$ | Yield CO | (wt % C) $CO_2$ | $C_3/H_4$ | $C_6H_6$ | Coke | Liquid |
|---|---|---|---|---|---|---|---|---|---|---|---|---|---|---|---|
| Forties VR | 28.0 | 1.29 | 0.23 | 0.36 | 335 | 58.4 | 9.43 | 0.06 | 20.68 | 6.32 | 1.85 | 1.11 | 1.57 | 3.8 | 36.5 |
| Forties VR | 28.0 | 1.29 | 0.23 | 0.36 | 350 | 61.8 | 11.5 | 0.25 | 21.10 | 5.93 | 2.91 | 1.10 | 1.64 | 4.36 | 33.4 |
| Arabian Light VR | 24.8 | 1.29 | 0.22 | 0.35 | 700 | 54.8 | 9.03 | 1.94 | 16.74 | 7.88 | 1.79 | 1.13 | 0.33 | 7.20 | 40.6 |
| Arabian Light VR | 28.3 | 1.40 | 0.22 | 0.36 | 690 | 47.5 | 10.47 | 1.30 | 14.69 | 8.05 | 1.14 | 1.15 | 0.80 | 2.98 | 45.9 | said inner housing mixes with the second feed stream before coming into contact with the second catalyst.

13. A process as claimed in claim 1 wherein the hydrocarbon feedstock of the second feed stream comprises a gaseous hydrocarbon, a heavy hydrocarbon or a mixture thereof.

14. A process as claimed in claim 13, wherein the hydrocarbon feedstock is ethane, propane, butane or mixtures thereof.

15. A process as claimed in claim 13, wherein the hydrocarbon feedstock is selected from the group consisting of naphtha, gas oil, vacuum gas oil, refinery residues, atmospheric residues, vacuum residues, crude oils, fuel oils and mixtures thereof.

16. A process as claimed in claim 1, wherein at least one of hydrogen, nitrogen, carbon monoxide, carbon dioxide and steam is included in the first or second feed stream as an additional feed component.

17. A process as claimed in claim 1, wherein the second catalyst comprises at least one metal selected from the group consisting of copper, tin, platinum and palladium.

* * * * *